(12) United States Patent
Frolov et al.

(10) Patent No.: US 6,943,015 B2
(45) Date of Patent: Sep. 13, 2005

(54) LARGE SCALE PRODUCTION OF PACKAGED ALPHAVIRUS REPLICONS

(76) Inventors: Ilya Frolov, 1024 Church, Galveston, TX (US) 77550; Elena Frolova, 1024 Church, Galveston, TX (US) 77550

( * ) Notice: Subject to any disclaimer, the term of this patent is extended or adjusted under 35 U.S.C. 154(b) by 0 days.

(21) Appl. No.: 10/735,046

(22) Filed: Dec. 12, 2003

(65) Prior Publication Data

US 2004/0235133 A1 Nov. 25, 2004

Related U.S. Application Data

(60) Provisional application No. 60/433,036, filed on Dec. 12, 2002.

(51) Int. Cl.[7] .............................. C12N 7/00; C12N 7/02; C12N 7/04; C12N 15/63; C12N 15/86; A61K 48/00; A61K 39/12
(52) U.S. Cl. ..................... 435/320.1; 435/236; 435/239; 435/455; 435/456; 435/457; 424/93.2; 424/199.1
(58) Field of Search ............................... 435/235.1, 456, 435/236, 239, 455, 457; 424/93.2, 199.1

(56) References Cited

PUBLICATIONS

Frolov, I. et al., "Selection of RNA Replicons Capable of Persistent Noncytopathic Replication of Mammalian Celss", 1999, J. Virol. vol. 73: pp. 3854–3865.*

Polo, J.M. et al., "Stable alphavirus packaging cell lines for Sindbis virus– and Semliki Forest virus–derived vectors", 1999, PNAS, vol. 96: pp. 4598–4603.*

Smerdou, C. et al., "Two–Helper RNA System for Production of Recombinant Semliki Forest Virus Particles", J. Virol., vol. 73: pp. 1092–1098.*

* cited by examiner

*Primary Examiner*—David Guzo
*Assistant Examiner*—Michael Burkhart
(74) *Attorney, Agent, or Firm*—Benjamin Aaron Adler

(57) ABSTRACT

Large-scale packaging of alphavirus replicons is accomplished by co-transfecting host cells with three RNA molecules: (1) an alphavirus replicon comprising a sequence encoding a heterologous protein; (2) a helper RNA encoding a capsid protein and (3) a helper RNA encoding two alphavirus glycoproteins. The helper RNAs contain cis-acting elements that allow efficient replication of the helper RNAs and their packaging into viral particles as well as packaging of replicon genomes. These populations of viral particles can be propagated at high titers in cell culture by infecting cells at high multiplicity. Propagation of packaged replicons at an escalating scale is useful for large-scale production of recombinant proteins and/or vaccine.

14 Claims, 17 Drawing Sheets

Schematic representation of Sindbis virus genome.

Packaging of Sindbis virus replicons into viral particles

Different types of Sindbis virus-based vectors.

SEQUENCE LISTING

<160> NUMBER OF SEQ ID NOS: 3

<210> SEQ ID NO 1
<211> LENGTH: 211
<212> TYPE: RNA
<213> ORGANISM: artificial sequence
<220> FEATURE:
<223> OTHER INFORMATION: cis-acting sequences for alphavirus genome
      replication and transcription of subgenomic
      RNA

<400> SEQUENCE: 1
auugacggcg uaguacacac uaugaaucaa acaguccgac caauugcacu          50
accaucacaa uggagaagcc aguaguaaac guagacugga accccagag          100 uccguuuguc gugcaacugc aaaaaagcuu cccgcaauuu gagguaguag         150
cacagcaggu cacuccaaau gaccaugcua augccagagc auuuucgcau         200
cuggccagua a                                                   211

<210> SEQ ID NO 2
<211> LENGTH: 170
<212> TYPE: DNA
<213> ORGANISM: Sindbis virus
<220> FEATURE:
<223> OTHER INFORMATION: 5' end of Sindbis virus subgenomic RNA with
      authentic translational enhancers

<400> SEQUENCE: 2
atagtcagca tagtacattt catctgacta atactacaac accaccaca           50 tgaatagagg attctttaac atgctcggcc gccgcccctt cccggccccc         100
actgccatgt ggaggccgcg ggaaaggagg caggcggccc cgatgcctgc         150
ccgcaacggg ctggcttctc                                          170

<210> SEQ ID NO 3
<211> LENGTH: 137
<212> TYPE: RNA
<213> ORGANISM: artificial sequence
<220> FEATURE:
<223> OTHER INFORMATION: 5' end of Sindbis virus subgenomic RNA with
      artificial translational enhancers

<400> SEQUENCE: 3
auagucagca uaguacauuu caucugacua auacuacaac accaccaca           50 ugaauagagg auucuuuaac augcucggcc gccgcgccuc uagaggcgcg         100
gcggccccga ugccugcccg caacgggcug gcuucuc                       137

LARGE SCALE PRODUCTION OF PACKAGED ALPHAVIRUS REPLICONS

CROSS-REFERENCE TO RELATED APPLICATION

This non-provisional application claims benefit of provisional U.S. Ser. No. 60/433,036, filed Dec. 12, 2002, now abandoned.

BACKGROUND OF THE INVENTION

1. Field of the Invention

The present invention relates generally to the study of alphaviruses such as Sindbis virus. More specifically, the present invention relates to an alphavirus packaging method useful in large scale production of recombinant vaccines or recombinant proteins.

2. Description of the Related Art

Progress in understanding the molecular mechanisms of alphavirus replication and pathogenesis has made possible their use as gene delivery and expression systems. Sindbis virus is a prototype and the least pathogenic member of the alphavirus genus. Sindbis virus can establish productive replication in a wide variety of cell lines of vertebrate and invertebrate origin. The biology of Sindbis virus has been better studied than that of any other alphavirus, and this fact favors its application as a vector for development of recombinant vaccines.

Sindbis virions are formed by three structural proteins: capsid protein and glycoproteins E1 and E2. A total of 240 molecules of the capsid protein assemble into an icosahedral nucleocapsid that packages the viral genomic RNA. The nucleocapsid is surrounded by a lipid envelope holding glycoprotein spikes. The spikes are present on the virion surface in an icosahedral lattice, and each contains three E1–E2 heterodimers.

The Sindbis virus genome is a single RNA molecule of positive polarity of almost 12 kb in size (FIG. 1). It mimics the structure of cellular mRNAs in that it contains both a 5' methylguanylate cap and a 3' polyadenylate tail. These features allow translation of viral proteins by host cell machinery immediately after release of the genome RNAs from the nucleocapsids. The 5' two-thirds of the genome is translated into the nonstructural proteins (nsPs) that comprise the viral components of the RNA-dependent RNA polymerase (RdRp) required for replication of the viral genome and transcription of the subgenomic RNA which is encoded by the 3' third of the genome. The subgenomic RNA is transcribed from the subgenomic promoter and translated into the viral structural proteins that form viral particles.

Alphaviruses as Vectors

The creation of infectious cDNA copies of several alphavirus genomes, identification of the cis-acting elements required for RNA replication and packaging, and the development of efficient methods for RNA transfection made possible use of alphaviruses as a gene delivery and expression system. It has been shown that the alphavirus genome can be divided into separate RNA fragments that complement each other's functions during intracellular replication (Weiss & Schlesinger, 1991).

A method of packaging Sindbis virus into infectious viral particle is shown in FIG. 2. Self-replicating Sindbis-specific RNAs (replicons) and helper RNAs (DH RNAs) are co-transfected into cells by electroporation. Replicons supply the replicative enzymes for their own replication and for that of helper genomes and for transcription of helper subgenomic RNA. Translation of the latter leads to production of viral structural proteins required for formation of viral particles. These particles contain predominantly replicon genomes, as helper RNAs lacking the packaging signals are packaged inefficiently. The average electroporation resulted in the production of $1-5 \times 10^9$ infectious particles with the usual titers of $5-10 \times 10^8$ Inf.u./ml.

On the next passage, particles deliver replicons into naive cells where replication begins. Initially, replicons serve as usual cellular messenger RNAs and express the nonstructural proteins forming the replicative complex. Next, replicon RNAs are used as templates for synthesis of a full-length minus-strand intermediate. The minus-strand intermediates then serve as templates for production of large quantities of positive-strand replicon RNAs. Within a few hours post infection, the replicative complexes perform $\sim 10^5$ fold amplification of the replicon genome. The subgenomic RNA coding the heterologous sequences is normally produced in a 10 fold excess to genome RNAs and becomes the main mRNA translated in the infected cells.

The infection does not spread to other cells because the alphavirus structural proteins required for virus particles formation are not expressed in the cells infected only by replicons. This made Sindbis virus-based and other alphavirus-based replicons a very attractive system for large-scale production of heterologous proteins. The expression systems were designed for Sindbis virus, Semliki Forest virus (SFV) and Venezuelan equine encephalitis virus (VEE). However, the use of Sindbis virus-based constructs instead of Venezuelan equine encephalitis-based or Semliki Forest virus-based replicons and packaging systems is advantageous because all of the experiments can be performed according to BSL2 regulations that dramatically increase the safety and efficiency of all the procedures.

However, initial experiments employing replicons and packaging systems revealed some phenomena that impaired application of alphavirus-based expression systems. It was noticed that the level of expression of the heterologous proteins by Sindbis virus replicons was lower than expected based on the level of accumulation of the subgenomic RNA. Replicons and helper RNAs also have a very high level of recombination that leads to formation of replication-competent viruses. Moreover, large-scale production of packaged replicons for vaccine applications was limited by the number of electroporations that could be performed.

It is an objective of the present invention to overcome these problems by developing new Sindbis virus vectors and packaging systems which are significantly different from the previously described ones. These new vectors can become prototypes for designing and manufacturing of recombinant vaccines against various pathogens.

SUMMARY OF THE INVENTION

Current methods for packaging of alphavirus replicons are based on generating helper-free stocks of replicon-containing viral particles that could be propagated only for research needs, and not on the industrial scale required for vaccinations. Importantly, co-electroporation of replicon and helper RNA encoding all the structural proteins can lead to recombination between these two RNAs and to formation of infectious alphaviruses.

The present invention provides an alternative approach for packaging of alphavirus replicons based on the application of two helper RNAs (FIG. 4). One of the helper RNAs encodes a capsid protein, the second helper RNA encodes two alphavirus glycoproteins (E1 and E2). These helper genomes contain newly designed artificial 5' cis-acting elements that promote not only efficient RNA replication, but also packaging of helpers into viral particles. Upon co-transfection into the cells with the replicon genome, the two helper genomes replicate effectively in the presence of the replicons. The replicons and the helper genomes are packaged into separate viral particles. High titers of viral particles are generated in vitro by infecting cells at high multiplicity of infection (MOI), whereas in vivo expression of the replicon genome is achieved by infection at low MOI due to very high number of cells in the animals.

This new method for packaging of alphavirus replicons has several important applications. Firstly, propagation of packaged replicons in tissue culture at an industrial scale allows further large-scale production of heterologous proteins. Proteins produced in mammalian cells are properly processed and post-translationally modified. The use of these proteins is greatly advantageous compared to the same proteins traditionally generated in insect cells using baculoviruses. Secondly, the present invention provides a very simple, inexpensive and efficient way to produce packaged alphavirus replicons up to $10^{14}$ infectious units that are equivalent to 10–100 millions doses of recombinant vaccine. The designed packaging system for alphavirus replicons will allow the generation of recombinant vaccines for emerging viral and other pathogens within a few weeks. Lastly, the method of the present invention makes possible packaging of alphavirus replicons into not only homologous structural proteins, but also structural proteins of heterologous alphaviruses as well.

Other and further aspects, features, and advantages of the present invention will be apparent from the following description of the presently preferred embodiments of the invention. These embodiments are given for the purpose of disclosure.

DETAILED DESCRIPTION OF THE INVENTION

Alphaviruses such as Sindbis virus, Semliki Forest virus and Venezuelan equine encephalitis virus have shown great promise as vectors for developing preventive and therapeutic vaccines against infectious diseases and cancer. Modified Sindbis or other alphavirus genomes are also used for production of heterologous recombinant proteins. Sindbis virus-based vectors routinely produce recombinant proteins more efficiently than any other viral or nonviral eucaryotic expression system, except possibly the baculoviruses.

The use of Sindbis virus as a vector provides a number of advantages. No human disease is associated with Sindbis virus, and the majority of the world population does not have preexisting antibodies to this virus. Replication of Sindbis virus occurs strictly in the cytoplasm of infected cells. In contrast to adeno- or retrovirus-based vectors, the genetic material of Sindbis virus cannot persist in the host cell genome. Sindbis virus grows productively to high titers in most commonly used cell lines of avian, mammalian and human origin, reaching titers of $10^9$–$10^{10}$ plaque-forming units per ml (PFU/ml) of culture media. The Sindbis virus genome has been cloned in cDNA form. The in vitro-synthesized RNA is highly infectious and leads to productive infection following transfection of vertebrate cells. The cDNA copy is not only a source of genetically homogeneous virus, but also provides an opportunity for engineering modifications into the viral RNA genome.

Figure 1:
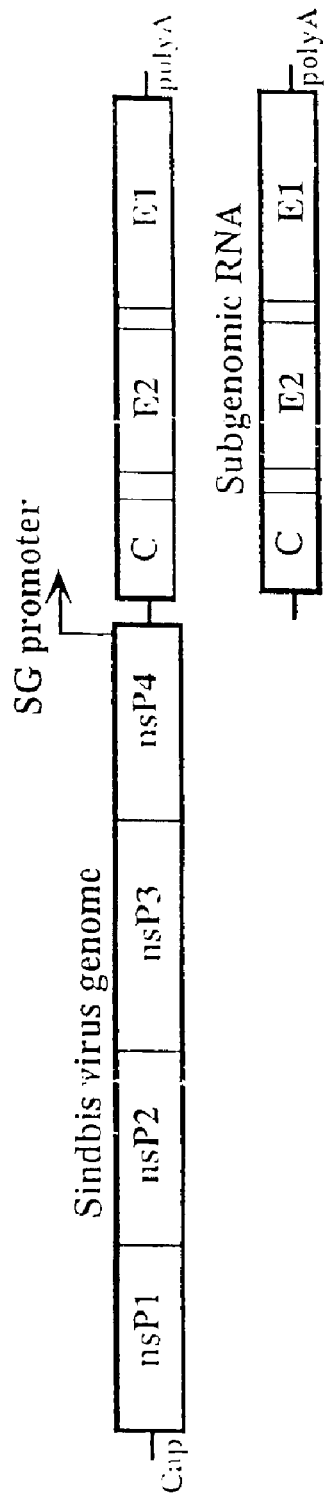
FIG. 1 is a schematic representation of the genome of Sindbis virus.
Figure 2:
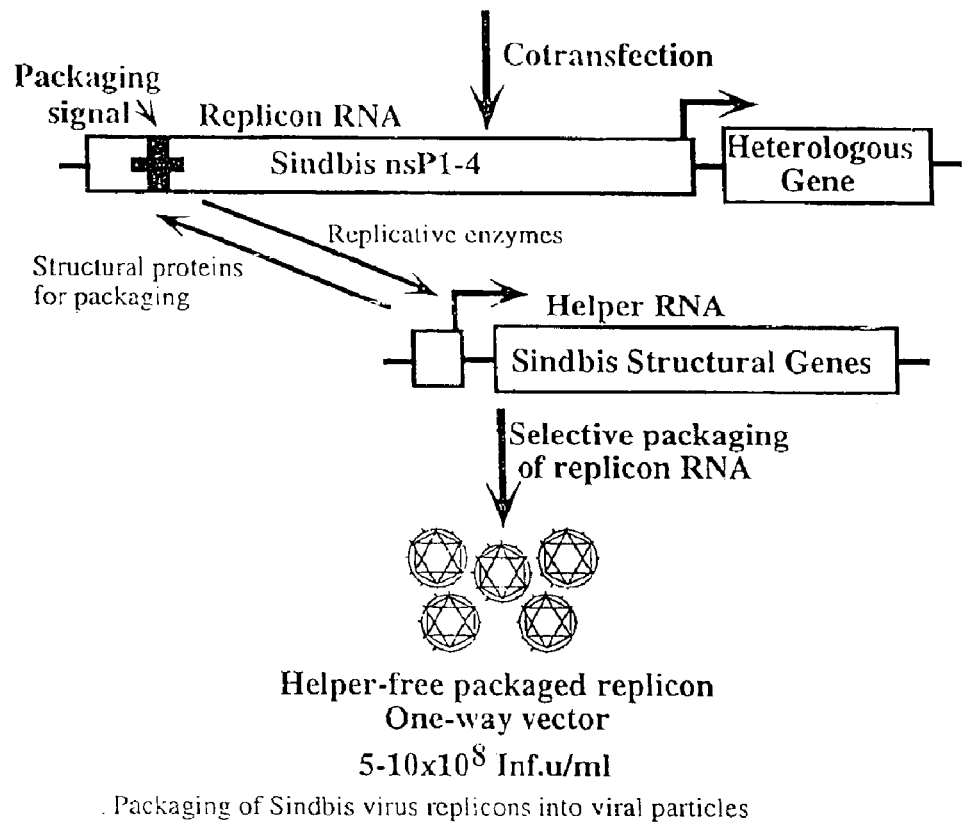
FIG. 2 shows a method of packaging Sindbis virus replicon into infectious viral particle using single helper RNA.
Figure 3:
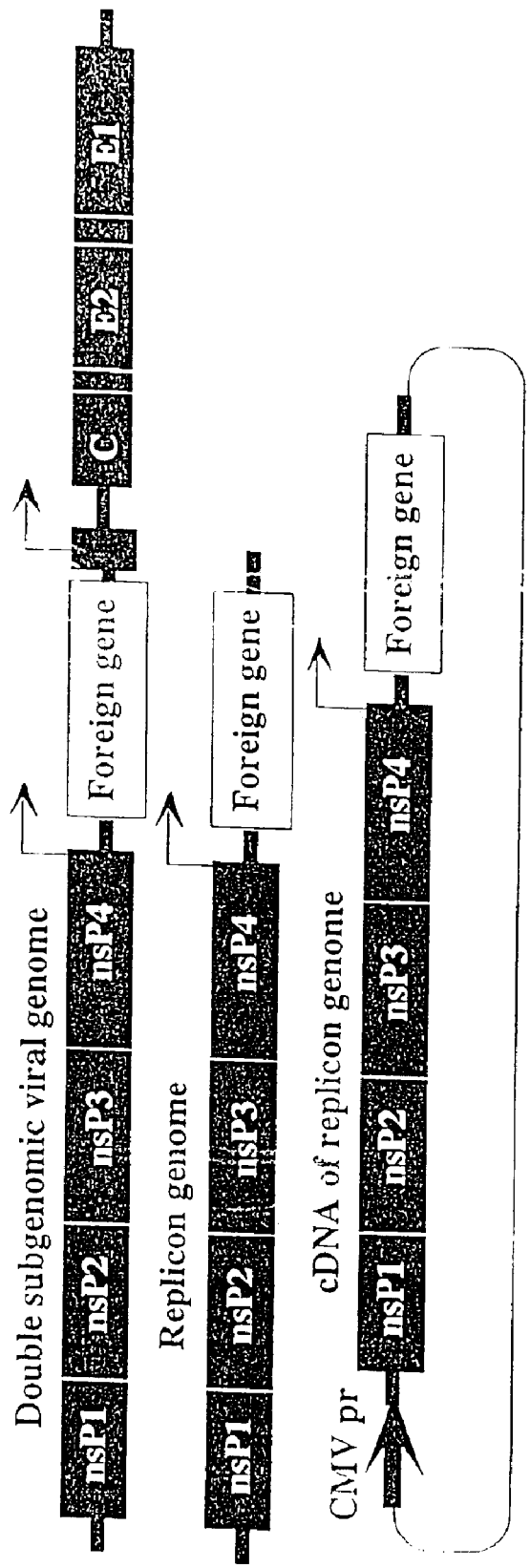
FIG. 3 shows different types of Sindbis virus-based vectors.

Currently, alphaviruses, and Sindbis virus in particular, are the safest, efficient and very flexible gene delivery and expression systems. Different Sindbis virus-based expression systems are demonstrated in FIG. 3. These vector genomes can be delivered into the cells as plasmids containing the cDNA of viral genome under control of commonly used CMV, RSV or other promoters. After transfection of these plasmids into the cells, the first RNA copies are synthesized by cellular RNA polymerase II and start self-replication in the cytoplasm. The vectors can also be transfected into the cells directly as in vitro-synthesized RNA. Alternatively, the vectors are packaged into viral particles and delivered to the cells by infection.

The main, commonly used competing technology for packaging of alphavirus replicons into viral particles is based on co-electroporation of replicon and one or two helper RNAs into mammalian cells. This procedure is expensive and labor-consuming and can be used for production of a very limited number of doses of vaccine. An industrial-scale electroporation procedure has not been developed yet.

Alternatively, alphavirus replicons can be packaged by using packaging cell lines that continuously express the helpers' genome RNAs in the cytoplasm. The disadvantage of this approach is that such cell lines can be developed only on BHK-21 cells and only after a very time-consuming procedure. In addition, titers of packaged replicons are 50 to 100-fold lower than the titers that are normally reached using co-transfection method.

Figure 4:
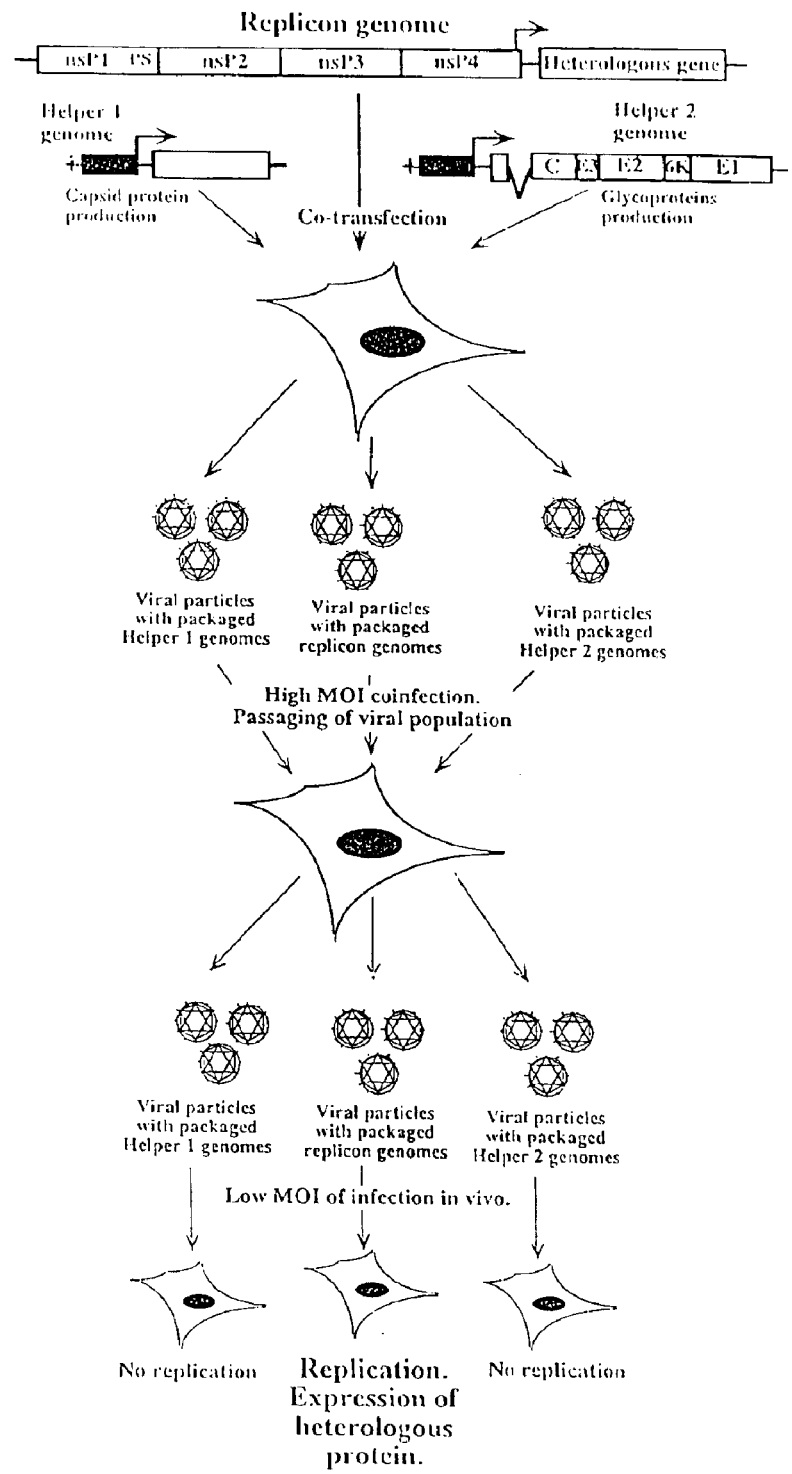
FIG. 4 depicts a method of large-scale production of alphaviruses using two helper RNAs at high and low multiplicity of infection.

The present invention provides an alternative approach for packaging of alphavirus replicons based on the application of two helper RNAs (FIG. 4). One of the helper encodes a capsid protein, the second helper encodes two alphavirus glycoproteins (E1 and E2). These three proteins form infectious viral particles. The helper genomes contain newly designed artificial 5' cis-acting elements that promote not only very efficient RNA replication but also packaging of helpers into viral particles despite of the lack of natural viral packaging signals. These 5' ends were developed on the basis of the 5' end of naturally occurring defective interfering RNA and contain sequence of tRNA$^{Asp}$ and replicational enhancer of Sindbis virus genome.

Upon transfection into the cells with the replicon genome, the two helper genomes replicate effectively in the presence of the replicons and are packaged into separate viral particles. The released viral population thus includes particles each containing a replicon genome, a capsid helper genome or a glycoprotein helper genome. On the next passage, infection will be productive (spreading) when all three kinds of particles infect the same cell and all three genomes (replicon and two helpers) replicate at the same time. This condition is easily achieved in tissue culture by using a reasonably high multiplicity of infection (5–10 infectious units of packaged replicon per cell).

At a low multiplicity of infection (<0.1 infectious units of packaged replicon per cell), the majority of cells are infected with one particle or either combination of two viral particles, and this excludes the possibility of productive infection. In the animals, because the MOI is <<1 viral particle per cell, the infection does not develop in a productive way. Infection of a particular cell in vivo with three particles containing a replicon and two helpers genomes is a highly unlikely event.

In summary, the present invention provides a system for production of packaged alphavirus replicons in practically unlimited amounts for their further application as vaccines against various pathogens of viral or other origins. Packaged replicons can be passaged in tissue culture by methods similar to ones that are normally applied to ordinary alphaviruses. When applied for vaccination, the packaged replicons can only perform a single-round of infection that leads to expression of heterologous genes encoded by the replicon subgenomic RNA and thus no disease is initiated.

Titers of packaged replicons approached 3–5×10$^8$ inf.u./ml after electroporation and 1–2×10$^9$ inf.u./ml after passage 1, 2 and 3 were performed with a dilution factor of 1:100. Two passages were sufficient to generate $10^{14}$ inf.u. of packaged replicons and this amount is equivalent to $10^7$–$10^8$ generally used doses of recombinant vaccine.

Moreover, large stocks of packaged replicons are also essential for production of proteins on an industrial scale. Replicons expressing heterologous genes in their subgenomic RNAs can be applied for production of properly processed and post-translationally modified proteins in mammalian cells. For some applications, infection of insect cells for protein production can be used as well.

As used herein, the term "alphavirus" refers to 26 currently recognized members of the Alphavirus genus of Togaviridae family.

As used herein, the term "replicon RNA or replicon genome" refers to self-replicating viral RNA that encodes all the nonstructural proteins forming replicative complex of enzymes and promoter elements (cis-acting elements) required for replication.

As used herein, the term "helper RNA or helper genome" refers to RNAs that can replicate in the presence of viral replicative enzymes and supply proteins not encoded by replicons and are required for viral particles formation.

As used herein, cis-acting elements that are required for RNA replication refers to RNA fragments that function as promoter elements recognized by viral replicative enzymes and are used to initiate plus- or minus-strand RNA synthesis.

As used herein, the term "replicational enhancer" refers to RNA sequences or secondary structures whose presence in the RNAs increases the level of their replication.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The present invention is directed to a method of large-scale production of high titer stocks of packaged alphavirus replicons using (i) a alphavirus replicon; (ii) a helper RNA comprising a sequence encoding an alphavirus capsid protein and (iii) a helper RNA comprising a sequence encoding the alphavirus glycoproteins E1 and E2. The alphavirus replicon usually contains sequence encoding a heterologous protein, whereas helper RNAs include cis-acting elements that allow efficient replication and packaging of helper RNAs. The replicon and the helper RNAs are delivered to the cells in plasmid form or in RNA form, and high titer of packaged viral particles (at least $5 \times 10^8$ infectious units per ml of media) can be maintained in tissue culture by infecting cells at high multiplicity of infection.

Generally, the alphavirus replicon is a Sindbis virus replicon, and the capsid and glycoproteins can be derived from Sindbis virus, Venezuelan Equine encephalitis virus, Ross River virus, or Semliki Forest virus. Representative cis-acting elements include tRNA$^{Asp}$ and replicational enhancer of Sindbis virus. The resulting high titer stock of viral particles can be used in large-scale production of recombinant proteins or vaccines.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cis-Acting Elements of Sindbis Virus Genome

One key element of this invention is the application of specific cis-acting elements in the helper genomes that allow very efficient replication of the helpers. The same RNA elements also function as efficient packaging signals. As a result, both replicons and helpers are efficiently packaged into viral particles.

Figure 5:
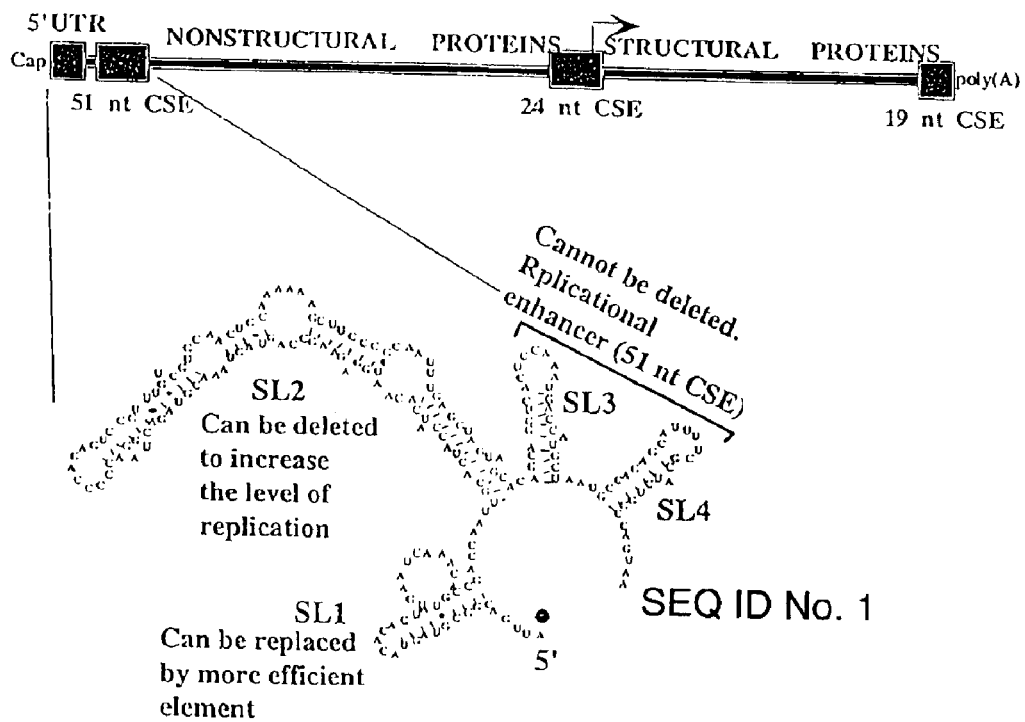
FIG. 5 shows cis-acting sequences that are required for alphavirus genome replication and transcription of subgenomic RNA.

The fine structure of the 5' cis-acting element of the Sindbis virus genome has been characterized (Frolov et al., 2001). This RNA element was of particular interest because it regulates the synthesis of both plus- and minus-strand RNA. The 5' cis-acting element, essential for viral RNA replication, has a modular structure and contains elements that could be classified as a part of the basal promoter represented by the 5' UTR (particularly SL1), and a replicational enhancer (the 51 nucleotides CSE) represented by the stable stem-loop structures SL3 and SL4 (FIG. 5). The 51 nucleotides CSE is not absolutely required for RNA replication in mammalian cells. Every stem-loop located downstream from SL1 could be deleted without completely abrogating the template activity of the RNA. However, the integrity of the enhancer increased the RNA replication 5–10 fold. Most importantly, deletion of the stem-loop SL1 strongly increased the replication of helper RNAs.

The 5' UTR of the Sindbis virus genome was found to be an essential component of the core promoters for both plus- and minus-strand RNA synthesis. Nevertheless, the Sindbis virus 5' UTR in helper RNAs can be replaced by tRNA$^{Asp}$, and this RNA replicates more efficiently than a similar helper with the authentic 5' UTR. Not only the integrity of the 3' UTR but also the combination of the 5' and 3' UTRs (derived from different alphavirus genomes) determines the level of RNA synthesis, particularly the minus-strand synthesis. The replacement of the Sindbis virus 3' UTR in the helper RNAs by the Semliki Forest virus counterpart significantly stimulated the RNA replication.

Initiation of replication is dependent on a number of other cis-acting RNA elements such as the presence of a poly(A)-tail in the 3' end and Cap in the 5' end, and the integrity of the 3' 19 nucleotides CSE and 5' UTR. The entirety of the 51 nucleotides CSE is also beneficial for the minus-strand RNA synthesis.

It is hypothesized that the Sindbis virus RNA-dependent RNA-polymerase interacts with the 5' end of the genome, and then is brought into position required for initiation at the 3' end of the genome by the cyclization of the template that is mediated by components of the cellular translational machinery. This hypothesis is not unique and joins a growing number of examples among animal RNA viruses. It was previously shown that flavivirus minus-strand synthesis required an interaction between the 5' and 3' ends of the flavivirus genome RNA resulted from the pairing of conserved complementary RNA sequences near the 5' and 3' ends. Alphavirus genome RNAs do not possess obvious complementary sequences, but direct RNA-RNA interactions could occur via "kissing" or by protein-stabilized, base-pairing interactions.

Thus far, the optimal combination of the 5' and 3' ends required for most efficient replication of the helper RNAs by Sindbis virus RNA-dependent RNA-polymerase is the tRNA$^{Asp}$+SL1sin+SL2sin on the 5' end and the 3' UTR derived from the genome of Semliki Forest virus. This template is utilized by Sindbis virus replicative enzymes more efficiently than RNA containing the homologous Sindbis virus 5' and 3' ends. Higher replication can lead, in turn, to a more efficient production of viral structural proteins and higher titers of packaged replicons. Other combinations of cis-acting elements can be applied for high replication of helper RNAs; however, the presence of tRNA$^{Asp}$ appears to be essential prerequisite.

Further Optimization of cis-Acting Elements for Helper RNAs

Figure 6:
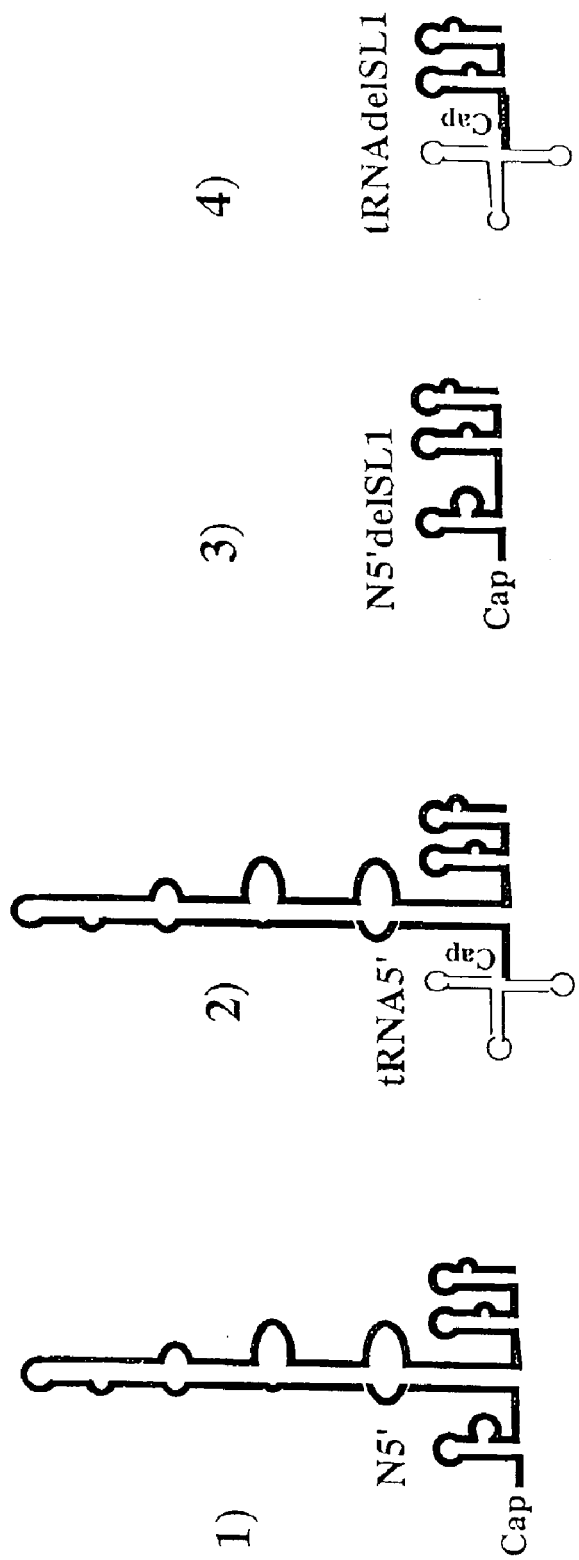
FIG. 6 shows 5' elements proposed for use in helper RNAs. N5', authentic 5' UTR and replicational enhancer of Sindbis virus; tRNA5', tRNA$^{Asp}$ and Sindbis virus replicational enhancer; N5'delSL1, authentic 5' UTR and Sindbis virus replicational enhancer lacking the stem-loop structure SL1; tRNAdelSL1, tRNA$^{Asp}$ and Sindbis virus replicational enhancer lacking SL1.

The 5' elements can be optimized by identifying sequences that support high level of helper RNAs replication and packaging but do not interfere with replication and packaging of Sindbis virus replicons. Representative examples of 5' elements that can be readily tested include (i) tRNA$^{Asp}$ and Sindbis virus replicational enhancer (tRNA5'); (ii) authentic 5' UTR and Sindbis virus replicational enhancer lacking the stem-loop structure SL1 (N5'delSL1); and (iii) tRNA$^{Asp}$ and Sindbis virus replicational enhancer lacking SL1 (tRNAdelSL1) (FIG. 6).

Initially, these helper RNAs will contain the Sindbis virus-derived 3' UTR. Helper RNAs containing the 3' UTRs derived from the Semliki Forest virus can also be constructed to test whether there is additional increase in efficiency of helper RNAs replication. The use of this heterologous 3' end has been shown to increase RNA replication to few folds compared to the authentic 3' UTR (Frolov et al., 2001).

Figure 7:
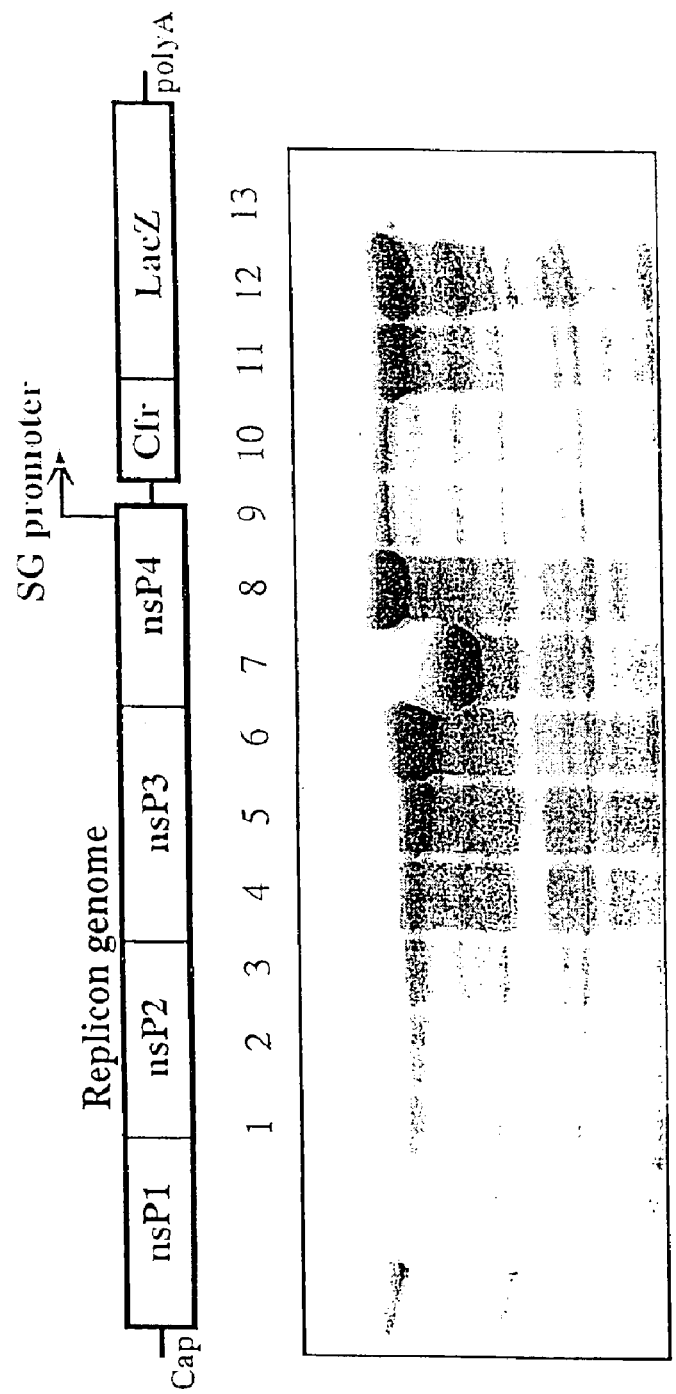
FIG. 7 identifies the translational enhancer in the Sindbis virus subgenomic RNA. The figure shows the expression of capsid-β-gal fusion protein by Sindbis virus replicons. Capsid-coding fragment of increasing length was fused in frame with b-gal-coding sequences (lanes 1–8) or in frame deletions were made in the amino terminal part of capsid in the construct N7 (lanes 9–11). Cell lysates were harvested 18 hours post infection. The gel was stained by Coomassie Brilliant Blue R-250.

EXAMPLE 2
Translational Enhancer And Expression of Heterologous Protein by Replicon Genome A series of Sindbis virus chimeric subgenomic RNAs in which a lacZ gene was fused in frame with the amino terminal fragment of Sindbis virus capsid-coding sequence of increasing length have been generated (Frolov and Schlesinger, 1996, 1994). Using these constructs, it was found that the amino terminal part of the capsid-coding gene (the 5' 275 nt) contained a structural RNA element that increased the efficiency of RNA translation 15–20 fold, making the expressed protein the major band on Coomassie-stained gels (FIG. 7). The main functional element of the enhancer was a G-C rich sequence located 28 nt downstream from the initiating AUG of Sindbis virus subgenomic RNA. That sequence was predicted to fold into a stable stem-loop structure. Mutations that decreased the G-C content of that fragment and destabilized the RNA secondary structure strongly affected the translation. The hairpin could not be moved upstream or downstream of its usual position without a significant decrease in translation efficiency. The enhancers appeared to function by slowing small ribosome subunits to scan RNA, which allowed translation-initiation factors to interact and form complexes competent for initiation of translation.

Figure 8:
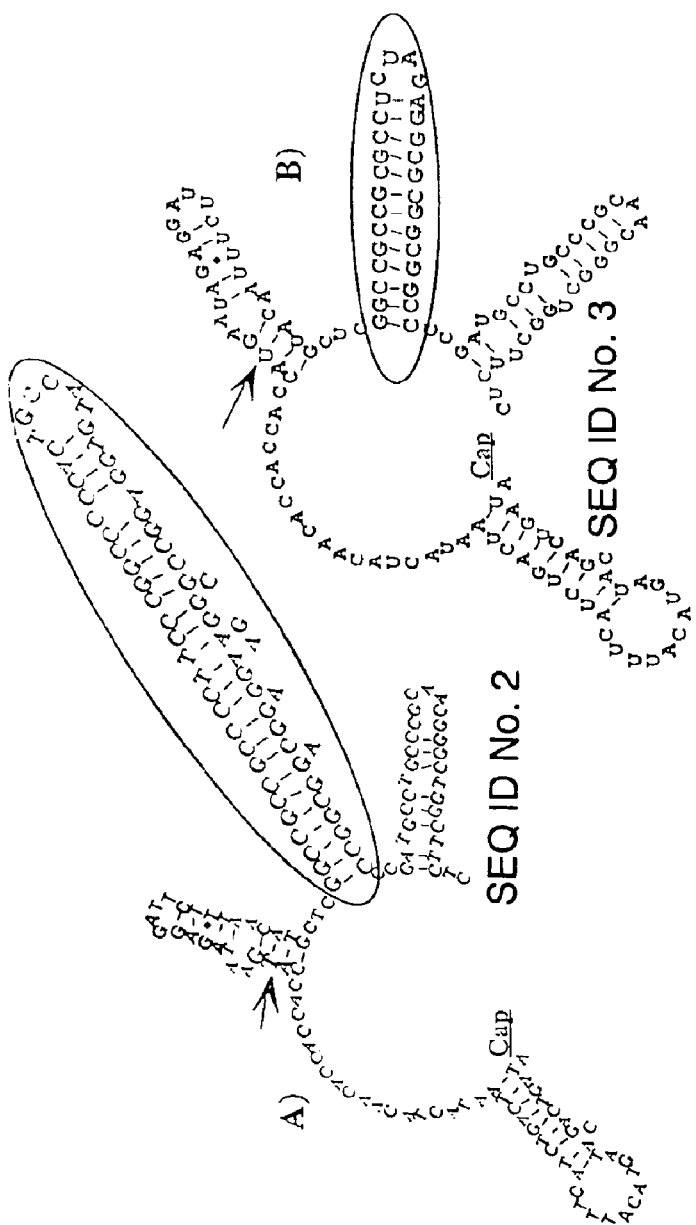
FIG. 8 shows the predicted secondary structure of the 5' end of Sindbis virus subgenomic RNAs with authentic (A) and artificial (B) translational enhancers (marked by ovals). The levels of β-gal expression in the cells infected with the replicons are shown in the table.

The effect of the stem-loop on translation was not sequence-specific; the natural stem-loop could be replaced by an artificial G-C rich stable hairpin that could enhance the translation equally well (FIG. 8). Similar stable RNA hairpins were found in the subgenomic RNAs of other alphaviruses, and their translation-enhancing effects have been confirmed. The enhancer was able to increase the efficiency of translation only in conditions of translational shutoff proceeding in the cells infected with alphaviruses. This made inhibition of host cell translation relevant only to cellular, but not to viral RNA which continued to function as efficient templates for production of structural proteins in the late stages of the infection.

Figure 9:
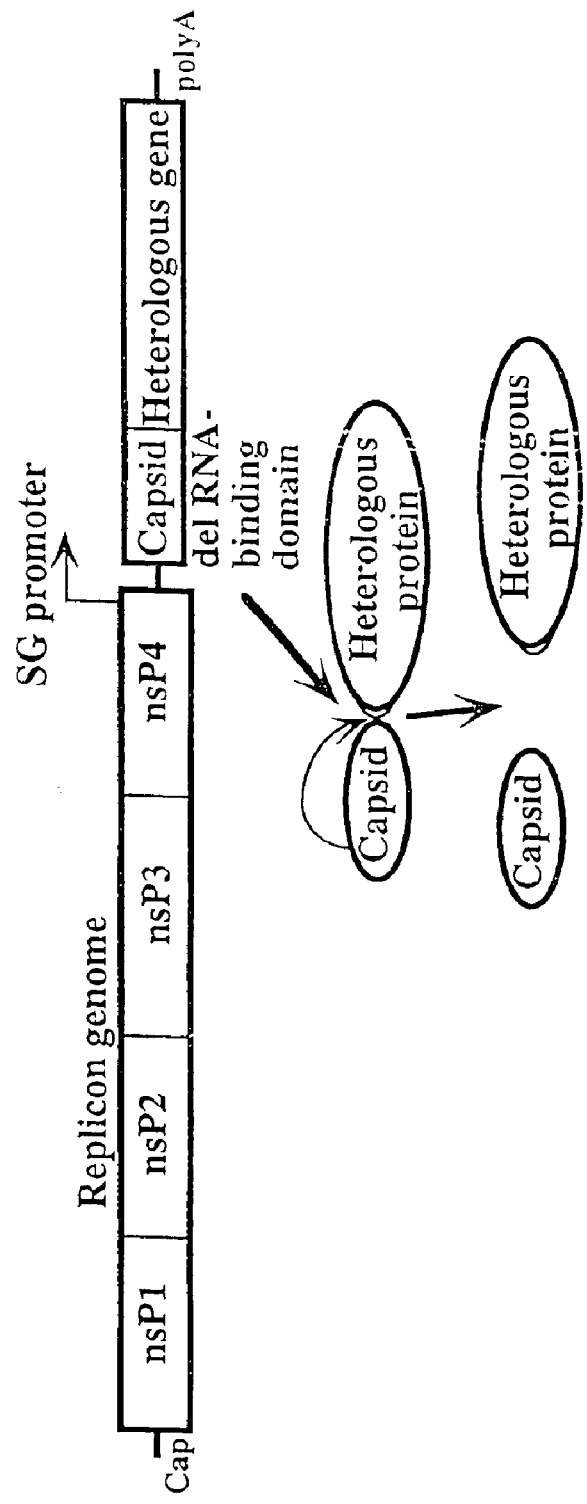
FIG. 9 shows the expression of heterologous gene by Sindbis virus replicon using translational enhancer.

These findings not only changed the understanding of the mechanism of virus-host cell interactions, but also made it possible to prepare new Sindbis virus-based vectors for expression of heterologous proteins. Replicon cassettes in which the Sindbis virus capsid was fused in frame with the heterologous genes can be constructed as shown in FIG. 9. During the translation stage, the capsid-coding RNA fragment functions as a translational enhancer. After synthesis, the capsid serves as autoprotease processing chimeric proteins into capsid and protein of interest.

EXAMPLE 3
Sindbis Virus Replicon With Reduced Cytopathogenicity

Sindbis replicons that could persist in some cell lines of vertebrate origin for an unlimited number of passages have been described recently (Agapov et al., 1998; Frolov et al., 1999). These self-replicating RNAs expressed a dominant selectable marker puromycin acetyltransferase. Their replication made cells resistant to puromycin and did not cause a detectable translational shutoff or other significant changes in cell biology. The inability of the replicons to induce cytopathic effect was due to mutations in the gene coding nonstructural protein, nsP2. One of the spontaneous adaptive mutations, $P_{726}$->L, was at the same position as the mutation previously found in the SIN-1 variant of Sindbis virus that also had a reduced level of cytopathogenicity. All of the mutants demonstrated an RNA replication level that was significantly lower than found for the replicons or viruses with the wt sequence of the nonstructural genes. These results suggested that the noncytopathic phenotype of normally cytopathic, self-replicating Sindbis virus RNAs was a result of the change in the nsP2 function(s).

The nsP2 is one of four nonstructural proteins encoded by the 5' two-thirds of alphavirus genomes. This protein is an essential component of the replicative complexes. It contains helicase and RNA triphosphatase activities required for RNA synthesis. This protein is also an autoprotease that orchestrates the sequential cleavage of nonstructural polyprotein precursor P1234. The nsP2 accumulates in the infected cells in 5–10 fold access to the nsP4, the catalytic subunit of the RNA-dependent RNA-polymerase. Moreover, in Semliki Forest virus-infected cells, a significant fraction of the nsP2 protein was shown to be transported to the nucleus. These facts suggested that this protein can have additional function(s) besides being a component of the viral RNA-dependent RNA polymerase.

Cells infected with the wild type Sindbis virus not only released high-titer virus progeny but also could not activate the transcription of interferons or any other genes. In contrast, the virus with a mutation in nsP2 did not suppress activation of the antiviral state, and the infected cells upregulated the transcription of 170 genes. A great fraction of these upregulated genes were represented either by cytokines or shown to be involved in the interferon response or proteasome degradation required for antigen presentation. It is expected that replicons with mutations in the nsP2 gene will not cause downregulation of cellular transcription and translation, thereby leading to a more efficient immune response to expressed heterologous proteins due to their efficient presentation to the immune system.

Considering the remarkable convergence of the mutations at position 726 of nsP2, several additional mutants at this locus in the context of the SINrep/Pac replicon and Sindbis virus genomes have been generated (Frolov et al., 1999). The original proline was substituted by ten different polar, hydrophobic and charged amino acids. A spectrum of RNA replication efficiencies, ranging from 100% to 1% of the wild type level, was observed in the BHK cells transfected by these mutants. Replicons with high levels of replication (>30% of the wt level) could not persist in BHK cells and caused cell death within a few days.

In mammalian cells infected with these nsP2 mutants, there was increased synthesis of 1) proteins involved in antigen processing and presentation, and 2) secretion of cytokines involved in stimulation of the immune response. These data suggested that expression systems based on mutant Sindbis virus genomes could be more efficient for generating an immune response to heterologous antigens than similar systems based on the genomes of the wild type virus.

Figure 10:
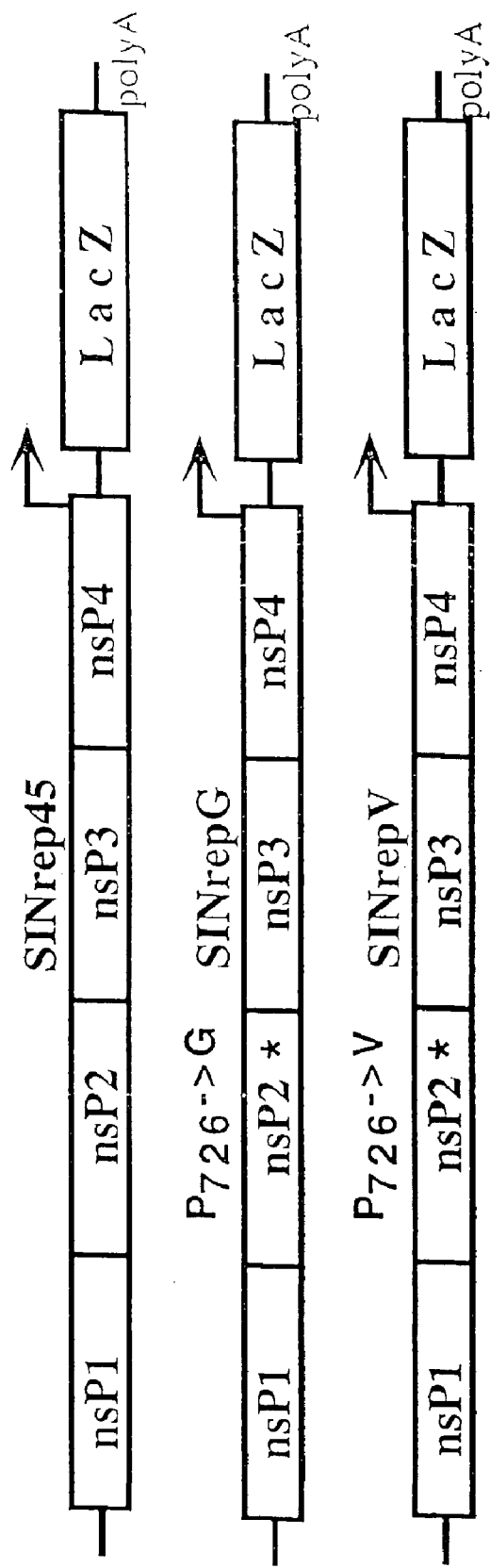
FIG. 10 is a schematic representation of Sindbis virus replicons with mutated nsP2 proteins. SINrep45 has a wild type sequence of the genes coding Sindbis virus nonstructural proteins. This replicon is very easy to work with, because it can be efficiently packaged into viral particles. It has a very high replication level that is very similar to that of the wild type Sindbis virus. SINrepG has essentially the same structure as SINrep45. It contains the only point mutation, $P_{726}$->G, in nsP2-coding gene that makes the replicon less cytopathic. Replication of this mutant does not cause translational and transcriptional shutoff in the infected cells. SINrepV is an intermediate variant between SINrep45 and SINrepG that also contains a point mutation $P_{726}$->V in the nsP2-coding gene. It replicates 4–6-fold less efficiently than does the wild type replicon, but causes noticeable changes in cell metabolism.

Examples of Sindbis virus replicons with mutated nsP2 proteins are shown in FIG. 10. All of the replicons are already cloned under the control of the SP6 promoter. SINrep45 has a wild type sequence of the genes coding Sindbis virus nonstructural proteins. This replicon is very easy to work with because it can be efficiently packaged into viral particles. It has a very high replication level that is very similar to that of the wild type Sindbis virus. SINrepG has essentially the same structure as SINrep45. It contains the only point mutation, $P_{726}$->G, in nsP2-coding gene that makes the replicon less cytopathic. Replication of this mutant does not cause translational and transcriptional shut-off in the infected cells. SINrepV is an intermediate variant between SINrep45 and SINrepG that also contains a point mutation $P_{726}$->V in the nsP2-coding gene. It replicates 4–6-fold less efficiently than does the wild type replicon, but causes noticeable changes in cell metabolism.

Figure 11:
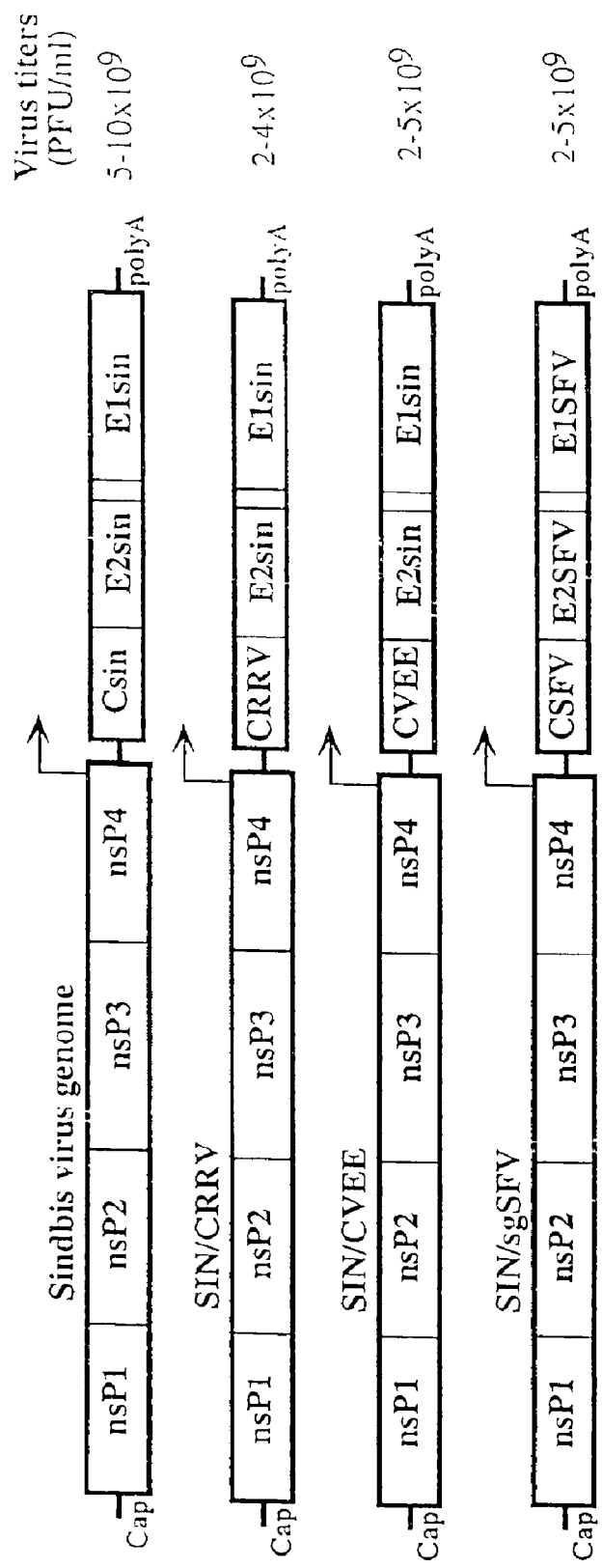
FIG. 11 shows the genomes and titers of recombinant Sindbis viruses expressing heterologous capsid proteins.

EXAMPLE 4
Packaging Sindbis Virus Genome With Structural Proteins of Heterologous Alphaviruses Packaging of alphavirus genomes into infectious virus particles is not as specific as it was believed to be. It has been shown that the Sindbis virus genomes or Sindbis virus-based replicons could be packaged into structural proteins of other alphaviruses almost as efficiently as into its own (Frolov et al., 1997a). Sindbis virus replicons and viral genomes were packaged into particles formed by structural proteins derived from Semliki Forest, Ross River, and Venezuelan Equine encephalitis viruses that belong to very distant antigenic groups. The heterologous helper RNAs used for packaging contained the Sindbis virus 5' and 3' cis-acting elements required for replication, as well as the Sindbis virus subgenomic promoter driving the expression of the subgenomic RNA (FIG. 11). These helpers packaged Sindbis virus replicons to essentially the same titers as Sindbis virus proteins expressed from similar constructs (Frolov et al., 1997b).

The most important consequence from these results is that packaging of Sindbis virus-specific RNAs into heterologous proteins opened a way to target packaged replicons into different tissues and to perform multiple vaccination procedures. The alphavirus genus contains almost 30 currently known members that can be divided into 4 or 6 antigenic groups. The homology in structural proteins between different antigenic groups does not exceed 40%, and alphaviruses induce only low levels of cross-reactive neutralizing antibodies upon infection.

It is very reasonable to expect that repeating vaccinations with packaged replicons would require the application of different envelopes. Since the structural proteins will be not exclusively Sindbis virus-derived, multiple vaccinations even in the presence of anti-Sindbis antibodies can be applied. Thus, it is proposed to package Sindbis virus replicons into envelopes of Venezuelan equine encephalitis virus, Ross River virus or Sindbis virus. Venezuelan equine encephalitis and Sindbis virus both are primarily targeted to human dendritic cells. These cells are the most potent antigen-presenting cell population and play a major role in the activation of both memory and naive T cells.

Helper RNAs for Packaging Into Heterologous Structural Proteins

Figure 12:
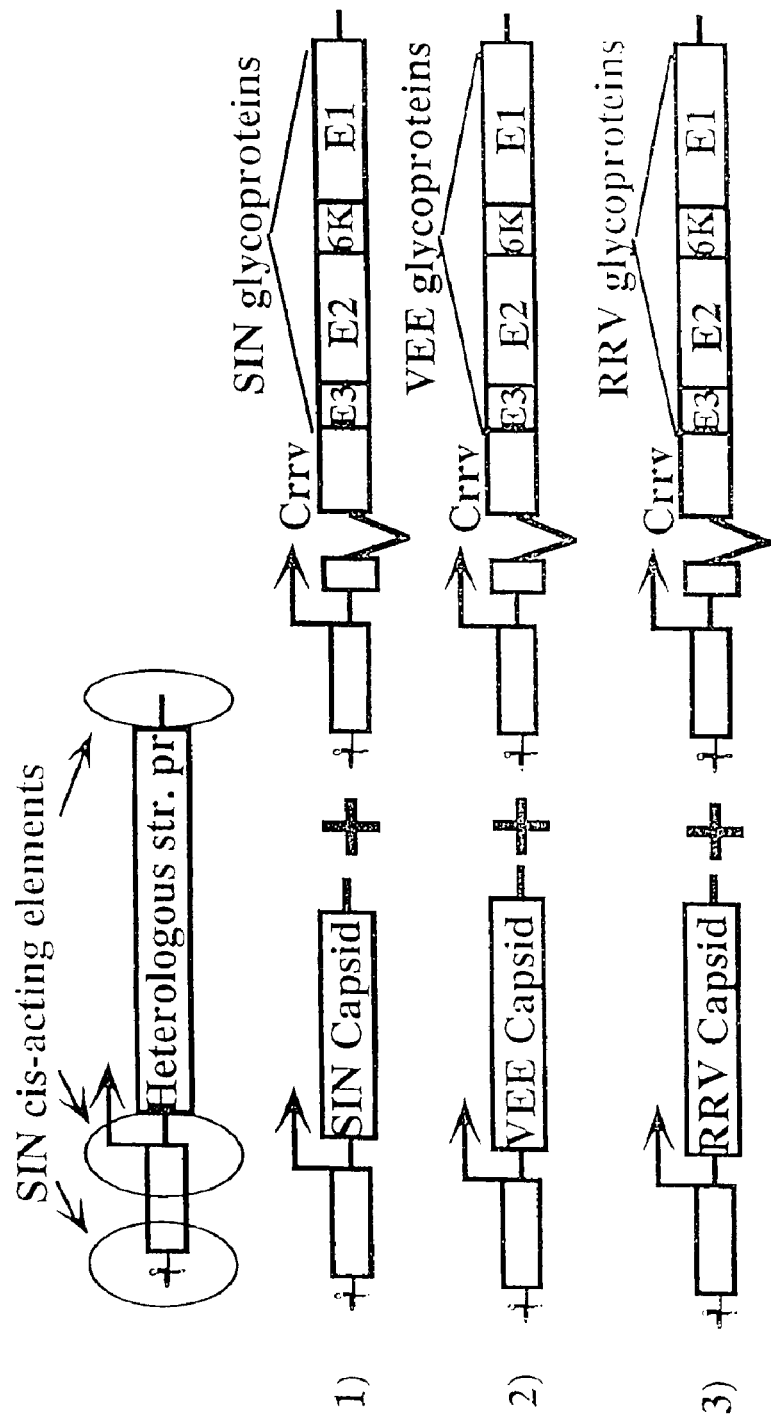
FIG. 12 is a schematic representation of alphavirus helper RNAs that are used for packaging the replicons with structural proteins of heterologous alphaviruses. (1), the SIN pair will package the Sindbis virus replicons into structural proteins of Sindbis virus variant that had high efficiency to infect human and mouse dendritic cells; (2) the Venezuelan equine encephalitis virus pair will package the Sindbis virus replicons into structural proteins of Venezuelan equine encephalitis virus strain 3908 that was previously found to efficiently infect mouse lymphoid tissues; (3) the RRV pair will package the Sindbis virus replicons into structural proteins of Ross River virus strain 6415 that is known to have a high tropism to muscle tissues.

The schemes of proposed helpers are demonstrated in FIG. 12. Each pair of helper RNAs will separately produce capsid and envelope glycoproteins. The SIN pair will package the Sindbis virus replicons into structural proteins of Sindbis virus variant that had high efficiency to infect human and mouse dendritic cells (Gardner et al., 2000). The Venezuelan Equine encephalitis virus pair will package the Sindbis virus replicons into structural proteins of Venezuelan Equine encephalitis virus strain 3908 that was previously found to efficiently infect mouse lymphoid tissues (Moncayo et al., 2001). The RRV pair will package the Sindbis virus replicons into structural proteins of Ross River virus strain 6415 that is known to have a high tropism to muscle tissues (Kuhn et al., 1991).

All of these helpers have similar genome organization and contain all Sindbis virus-specific cis-acting elements required for efficient replication and transcription of the subgenomic RNA. These elements include the 5' end sequence derived from the naturally occurring DI RNA of Sindbis virus, followed by replicational enhancer, promoter of Sindbis virus subgenomic RNA, structural proteins of Sindbis virus or other viruses and 3' UTR of Sindbis virus genome (Frolov et al., 2001; Monroe and Schlesinger, 1983, 1984). Sindbis virus and Ross River virus helpers have previously been constructed for use in different studies (Frolov et al., 1996, 1997a). Helper expressing Venezuelan Equine encephalitis virus capsid has also been created.

Helper expressing Venezuelan Equine encephalitis virus (VEE) glycoproteins can be designed on the base of Venezuelan Equine encephalitis virus cDNA infectious clone kindly provided by Dr. Scott Weaver (UTMB, Galveston). A modified capsid-coding sequence of Ross River virus is included in all of the helpers expressing glycoproteins. This capsid sequence functions as a translational enhancer that significantly upregulates translation of subgenomic RNA and stimulates formation of viral particles at least 10 fold (Frolov et al., 1997a). It is also believed that the capsid protein targets polysomes to the proper cellular compartment so that the following glycoproteins are efficiently processed, folded and transported. This Ross River virus capsid contains a deletion of the whole RNA-binding motif and is not involved in RNA packaging. Packaging systems for Venezuelan Equine encephalitis virus-based replicons that do not include capsid sequences upstream of glycoprotein-coding genes are 20–50-fold less efficient than similar systems designed for Sindbis virus and Semliki Forest virus replicons that include the capsid enhancers (Pushko et al., 1997).

EXAMPLE 5
Determining the Packaging Efficiencies of Different Helper RNAs

The following set of experiments would generate information about the abilities of different helper RNAs to i) replicate, ii) interfere with replication of replicons, iii) package replicons into viral particles and iv) to package themselves. Based on these results, the best combination of helpers RNA and replicons can be chosen for large-scale production of packaged viruses. The optimal helpers are expected to package replicons to concentration of more than $5 \times 10^8$ inf.u./ml and package themselves to the same or only few fold higher concentration.

After co-transfection with the replicons and two helper RNAs, the cells are divided between four 35-mm dishes and incubated at 37° C. In one dish, the culture media is harvested after the development of cytopathic effect and is used to determine the titer of packaged replicon. Naive BHK-21 cells are infected with different dilutions of the harvested samples and covered with agarose. After incubation for 24 hours at 37° C., the agarose is removed and the cells are fixed with methanol and stained.

The second and third dishes are used to determine the relative levels of replication of helper and replicon RNAs. Culture media is replaced 2 and 10 hours post-transfection by the same media supplemented with 10% FBS, 20 $\mu$Ci/ml of [$^3$H]uridine and 1 $\mu$g/ml of Act.D. The cells are incubated for 3 hours at 37° C. and RNA is isolated by TRizol using standard protocol recommended by the manufacturer (Gibco-BRL). RNAs are analyzed by agarose gel electrophoresis following denaturing with glyoxal in dimethyl sulfoxide. Gels are impregnated with 2,5-diphenyloxazol, dried and the RNA bands can be visualized by autoradiography. These bands are excited and the amount of radioactivity are determined by liquid scintillation counting.

The fourth dish is used to analyze the RNAs packaged into viral particles. Four hours post-electroporation, the cells are labeled with [$^3$H]uridine (20 $\mu$Ci/ml) for 24 hours at 37° C. Then the media is harvested, clarified by low-speed centrifugation, and viral particles can be pelleted by ultracentrifugation (e.g. SW-50.1 rotor, 45,000 rpm, 4° C., 1 hour). RNAs are extracted from viral particles by TRizol using a standard procedure, denatured and analyzed by agarose gel electrophoresis as described above. The relative levels of packaging can be determined based on radioactivity incorporated into different species of packaged RNAs and their length.

A possible pitfall in the present packaging method is that different helper RNAs may be packaged into viral particles with different efficiencies due to their different sizes. Capsid-expressing helper RNA is almost four-fold shorter than glycoproteins-coding helper genome and can have a significantly lower ability to be packaged into viral particles. This potential problem can be overcome by the following three modifications. Firstly, capsid-expressing helper can be designed to have the size similar to that of the 26S subgenomic RNA. It will contain terminating codon after capsid-coding sequence and the deletion between capsid and E2 genes to avoid formation of viable recombinants between capsid and glycoprotein helper RNAs.

Secondly, different 5' or 3' cis-acting elements can be used to make the capsid-expressing helpers replicate at a higher rate than that of glycoprotein-expressing helpers. Thirdly, helper RNA can be designed to contain packaging signals that can increase the level of packaging without changing the level of RNA replication. These signals were previously identified for Sindbis virus and RRV (Frolov et al., 1997b; Weiss et al., 1989).

EXAMPLE 6
Large-Scale Packaging of Replicons And Propagation of Replicon-Containing Particles The development of any vaccine raises the question of its large-scale production at reasonable expense. Live attenuated vaccines replicate upon inoculation and thus require dramatically less virus material (particles) per immunizing dose than do inactivated vaccines. However, live attenuated vaccine strains are not available for a number of significant viral pathogens, and in particular, there is no live attenuated vaccine for emerging viral infections. Large-scale production of inactivated vaccines that require BSL3 or BSL4 facilities is very problematic as well.

Currently, there is no system for industrial-scale production of packaged alphavirus replicons on the market. The methods of the present invention provide a simple, inexpensive and efficient way to produce packaged alphavirus replicons up to $10^{14}$ infectious units that are equivalent to 10–100 millions doses of recombinant vaccine.

The methodology disclosed herein comprises the following elements: (1) packaged replicons should be passaged on an escalating scale in tissue culture in a way similar to that used for wild-type alphaviruses; (2) in order to generate large stocks of packaged replicons, passaging should be performed at least at 1:100 dilution on each passage; (3) titers of packaged replicons should be at least $5\times10^8$ infectious units per ml of media; and (4) production of replicon-containing viral particles should be above 1000 infectious units per cell.

Optimization For the Propagation of Packaged Replicons

Optimal protocol for passaging replicons in tissue culture on an escalating scale can be determined as follows. Preliminary experiments performed with SINrep/LacZ replicon demonstrated that passaging is a real possibility. Results from the following experiments would optimize the passaging conditions for the components of the replicon-helper system disclosed herein.

Replicon containing the translational enhancers described above and helpers with the cis-acting elements disclosed herein can be synthesized in vitro by SP6 RNA polymerase, and 4 $\mu$g of each RNA can be electroporated into BHK-21 cells. The transfected cells are seeded into 100-mm dish (8 ml) to prepare viral stock and into 35-mm dishes (2 ml). In the 100-mm dish, culture media is harvested upon development of cytopathic effects. In the 35-mm dish, 20 $\mu$Ci/ml [$^3$H]uridine is added 2 hours post infection, and the labeling is performed until harvesting the media in a large dish. The $^3$H-labelled viral particles are pelleted by ultracentrifugation and packaged RNAs are analyzed in the conditions described above. These results of RNA analysis can be compared to the results generated in the next passages. The concentrations of packaged replicons in the media harvested from the 100-mm dish can also be determined using the procedure described above.

Next, $3\times10^6$ naive BHK-21 cells in 100-mm dishes or $5\times10^5$ cells in 35-mm dishes are infected at MOI 0.1, 1, 10 and 50 inf.u./cell. Similar to the experiment described above for electroporation, media from the large dish is used to analyze titers of packaged replicons, and that from the small dish is used to label RNA in the viral particles to analyze ratio of packaged replicon and helpers' genomes. The sample with the best ratio (~1:1:1) will be used for the next passage at MOI used for its preparation. After these detailed experiments, the most important characteristic of passaging in culture, i.e. the MOI that is required for keeping the ratio of the replicon RNA: Capsid helper RNA: Glycoproteins helper RNA in viral particles close to 1:1:1 will be known.

Figure 13:
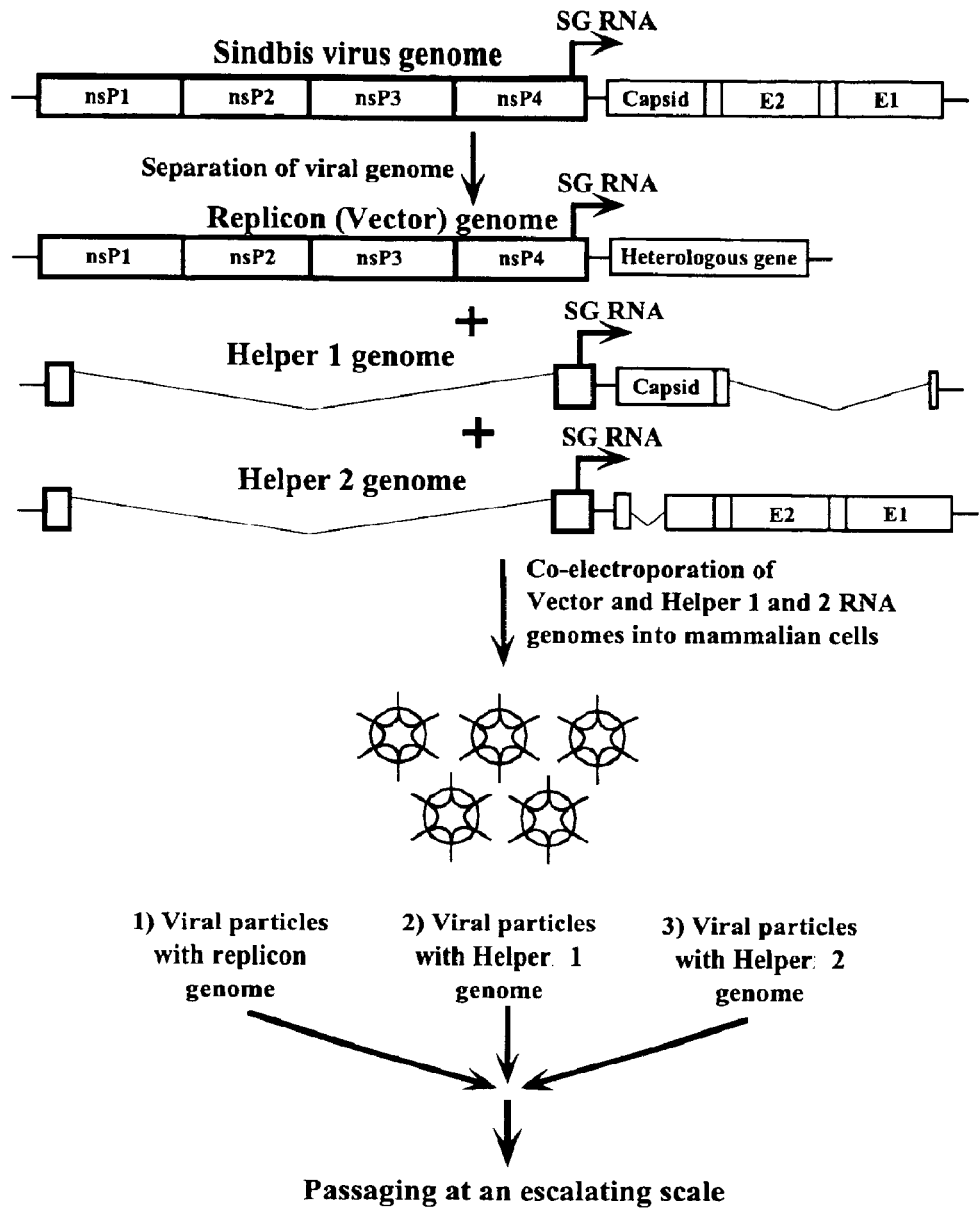
FIG. 13 is a schematic representation of replicon genome and Helper 1 and Helper 2 genomes. After co-transfection of replicon and helpers' in vitro-synthesized RNAs into the cells, they complement each others' functions, are capable of replication and produce all the proteins required for RNA replication, transcription of the subgenomic RNA and viral particles formation. Cells release combination of viral particles that contained replicon and both helpers' RNAs packaged separately. These populations of particles can be passaged at an escalating scale.

FIG. 13 is a schematic representation of replicon genome and Helper 1 and Helper 2 genomes. After co-transfection of replicon and helpers' in vitro-synthesized RNAs into the cells, they complement each others' functions, are capable of replication and produce all the proteins required for RNA replication, transcription of the subgenomic RNA and viral particles formation. Cells release combination of viral particles that contained replicon and both helpers' RNAs packaged separately. These populations of particles can be passaged at an escalating scale.

Figure 14:
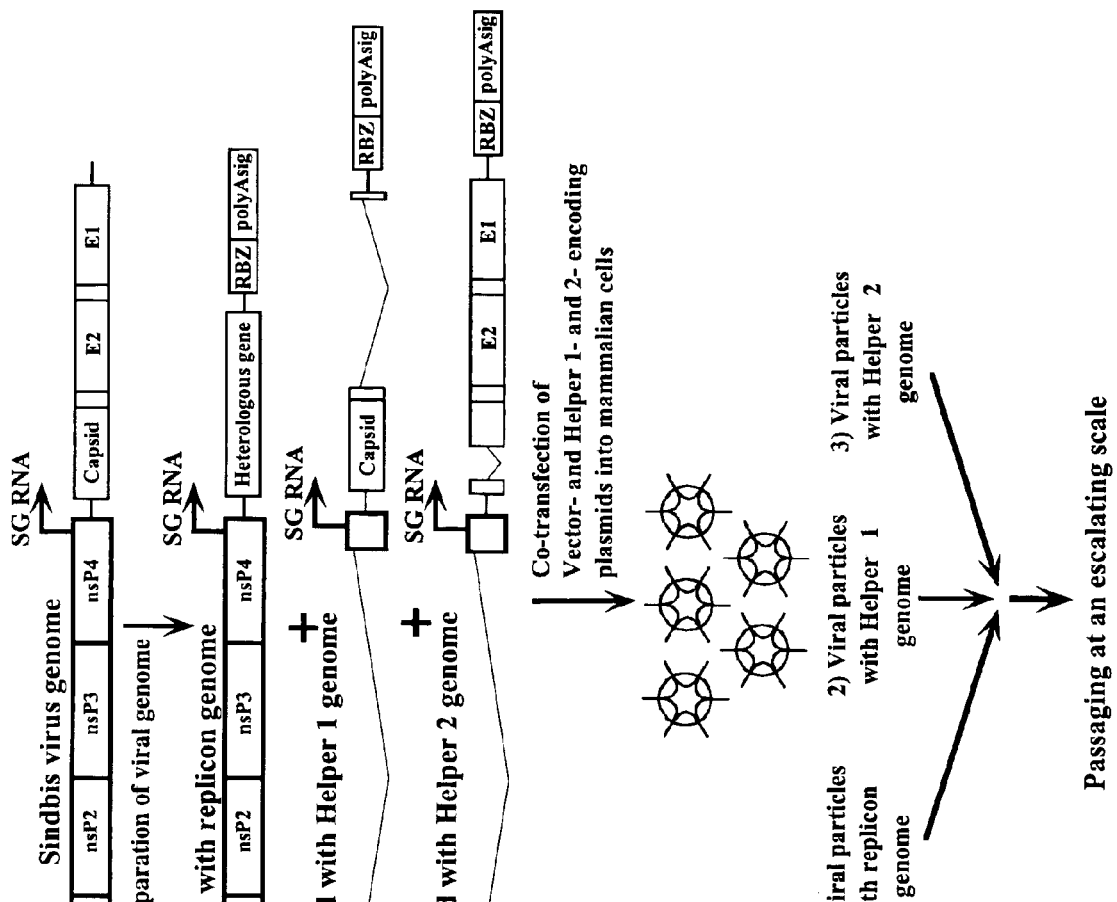
FIG. 14 shows the replicon and helpers' genomes can be delivered into the cells in a plasmid form. In this case, the genomes are cloned under control of RSV promoter and contain ribozyme downstream of poly(A) followed by polyadenylation signal of SV40. Transfection of all three plasmids into the cells leads to synthesis of replicon and helper RNAs by cellular RNA polymerase, followed by their replication and release of viral particles containing replicon and both helper genomes.

FIG. 14 shows the replicon and helpers' genomes can be delivered into the cells in a plasmid form. In this case, the genomes are cloned under control of RSV promoter and contain ribozyme downstream of poly(A) followed by polyadenylation signal of SV40. Transfection of all three plasmids into the cells leads to synthesis of replicon and helper RNAs by cellular RNA polymerase, followed by their replication and release of viral particles containing replicon and both helper genomes.

Figure 15:
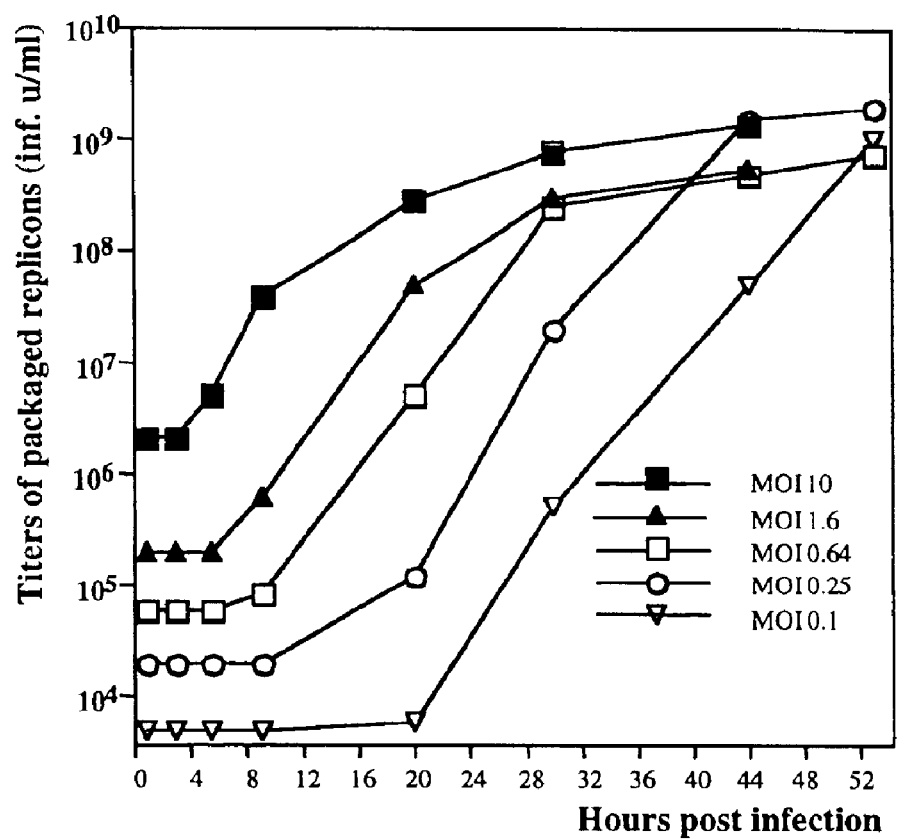
FIG. 15 shows an analysis of replicon-containing viral particles release into the media. Viral stock generated after passage 1 (transfection is considered to be passage 0) after co-transfection of vector and both helper RNAs into BHK-21 cells was used to infect naive BHK-21 cells at indicated multiplicities. At the indicated times, media were replaced and titers of replicon-containing particles were determined.

FIG. 15 shows an analysis of replicon-containing viral particles release into the media. Viral stock generated after passage 1 (transfection is considered to be passage 0) after co-transfection of vector and both helper RNAs into BHK-21 cells was used to infect naive BHK-21 cells at indicated multiplicities. At the indicated times, media were replaced and titers of replicon-containing particles were determined.

Tables 1 and 2 demonstrate passaging of replicons at an escalating scale.

Figure 16:
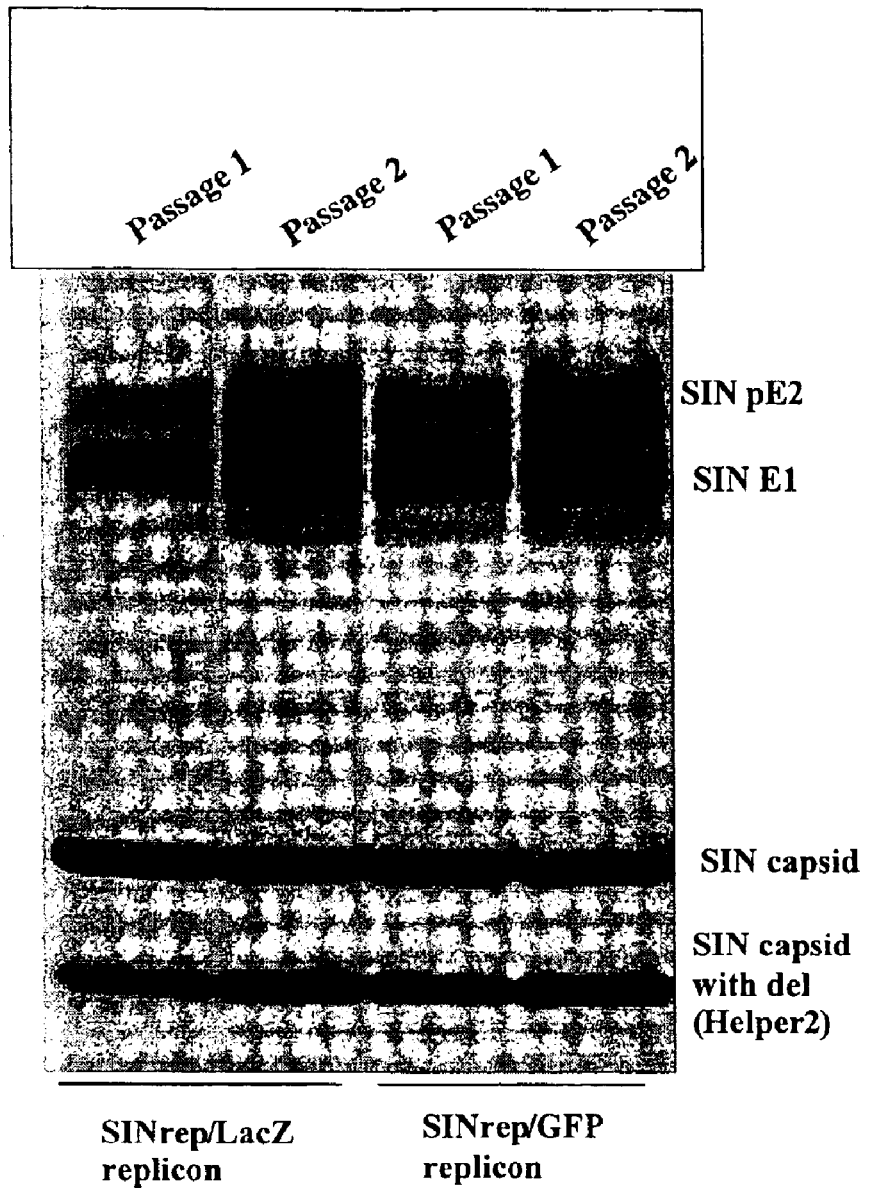
FIG. 16 shows the synthesis of Sindbis virus-specific structural proteins in the cells infected with virus particles harvested after electroporation (passage 1) and after passage 1 (passage 2). BHK-21 cells were infected at an MOI of 20 inf.u/cell and proteins were pulse-labeled 16 h post infection with [$^{35}$S]methionine and analyzed on sodium dodecyl sulfate-10% polyacrylamide gel. Gel was dried and autoradiographed. Sindbis structural proteins produced by replicating helpers are indicated. In this experiment two replicons, SINrep/LacZ and SINrep/GFP, producing β-galactosidase and green fluorescent protein, respectively, were used.

FIG. 16 shows the synthesis of Sindbis virus-specific structural proteins in the cells infected with virus particles harvested after electroporation (passage 1) and after passage 1 (passage 2). BHK-21 cells were infected at an MOI of 20 inf.u/cell and proteins were pulse-labeled 16 h post infection with [$^{35}$S]methionine and analyzed on sodium dodecyl sulfate-10% polyacrylamide gel. Gel was dried and autoradiographed. Sindbis structural proteins produced by replicating helpers are indicated. In this experiment two replicons, SINrep/LacZ and SINrep/GFP, producing β-galactosidase and green fluorescent protein, respectively, were used.

Figure 17:
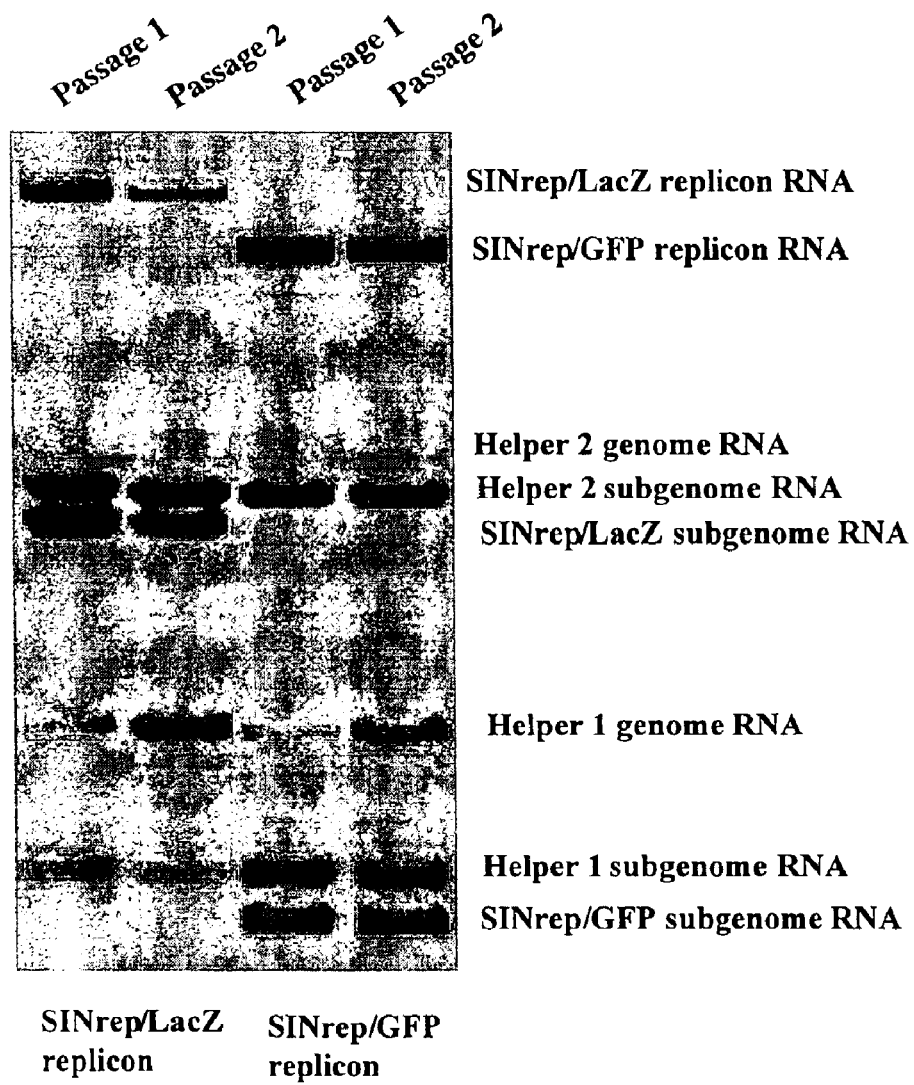
FIG. 17 shows the synthesis of Sindbis virus-specific RNAs in the cells infected with virus particles harvested after electroporation (passage 1) and after passage 1 (passage 2). BHK-21 cells were infected at an MOI of 20 inf.u/cell and RNAs were metabolically labeled with [$^3$H] uridine between 16 and 20 hours post infection. RNAs were then analyzed by agarose RNA gel electrophoresis. Positions of replicon and helpers' genomic and subgenomic RNAs are indicated. In this experiment two replicons, SINrep/LacZ and SINrep/GFP, producing β-galactosidase and green fluorescent protein, respectively, were used.

FIG. 17 shows the synthesis of Sindbis virus-specific RNAs in the cells infected with virus particles harvested after electroporation (passage 1) and after passage 1 (passage 2). BHK-21 cells were infected at an MOI of 20 inf.u/cell and RNAs were metabolically labeled with [$^3$H] uridine between 16 and 20 hours post infection. RNAs were then analyzed by agarose RNA gel electrophoresis. Positions of replicon and helpers' genomic and subgenomic RNAs are indicated. In this experiment two replicons, SINrep/LacZ and SINrep/GFP, producing β-galactosidase and green fluorescent protein, respectively, were used.

TABLE 1

Passaging of Viral Populations In BHK-21 Cells After Co-Transfection of Replicons' And Helper RNAs

| Passage | Titer of Replicon-Containing Viral Particles | Volumne | Total Amount of Replicon-Containing Viral Particles |
| --- | --- | --- | --- |
| Co-transfection | 2–5 × 10$^8$ inf.u/ml | 10 ml | 2–5 × 10$^9$ |
| Passage 1 | 2–5 × 10$^8$ inf.u/ml | 1000 ml | 2–5 × 10$^{11}$ |
| Passage 2 | 2–5 × 10$^8$ inf.u/ml | 100 l. | 2–5 × 10$^{13}$ |

TABLE 2

Passaging of Viral Populations In BHK-21 Cells After Co-Transfection of Replicons' And Helper Genome-Encoding Plasmids

| Passage | Titer of Replicon-Containing Viral Particles | Volumne | Total Amount of Replicon-Containing Viral Particles |
| --- | --- | --- | --- |
| Co-transfection | 1–2 × 10$^9$ inf.u/ml | 10 ml | 1–2 × 10$^{10}$ |
| Passage 1 | 2–5 × 10$^8$ inf.u/ml | 5000 ml | 1–2.5 × 10$^{12}$ |
| Passage 2 | 2–5 × 10$^8$ inf.u/ml | 500 l. | 1–2.5 × 10$^{14}$ |

The present invention demonstrates that primary stocks of virus particles that contain three genomes (replicon, helper 1 and helper 2) can be prepared either by RNA or DNA transfection (FIGS. 13 and 14). These primary virus stocks, initially generated by DNA or RNA transfection, can be passaged at dilutions between 1:100 and 1:1000 (FIG. 15) and cells remain capaple of producing more than 1000 replicon-containing particles per cell. After two passages that can be performed within one week, virus stocks approaching 10$^{13}$–10$^{14}$ replicon-containing particles can be made. This number of particles is equivalent to at least 10 mln doses of vaccine (Tables 1 and 2). Packaging and replication of replicon and both helper genomes into viral particles was confirmed by detecting all of the RNAs (replicon and helpers' genomes and their subgenomic RNAs) and proteins (structural proteins of Sindbis virus) in the infected cells FIGS. 16 and 17. All the experiments were performed using two replicons expressing different cloned genes.

The following references were cited herein:

Agapov et al., (1998) Noncytopathic Sindbis virus RNA vectors for heterologous gene expression. Proc. Natl. Acad. Sci. USA. 95:12989–12994.

Frolov et al., (2001) Cis-acting RNA elements at the 5' end of Sindbis virus genome RNA regulate minus- and plus-strand RNA synthesis. RNA 7:1638–51.

Frolov et al., (1999) Selection of RNA replicons capable of persistent noncytopathic replication in mammalian cells. J. Virol. 73:3854–3865.

Frolov et al., (1997a) Sindbis virus replicons and Sindbis virus: assembly of chimeras and of particles deficient in virus RNA. J Virol. 71:2819–2829.

Frolov et al., (1997b) Packaging signals in alphaviruses. J Virol. 71:248–58.

Frolov et al., (1996) Alphavirus-based expression systems: strategies and applications. Proc. Natl. Acad. Sci. USA. 93:11371–11377.

Frolov and Schlesinge, (1996) Translation of Sindbis virus mRNA: analysis of sequences downstream of the initiating AUG codon that enhance translation. J. Virol. 70:1182–90.

Frolov and Schlesinger, (1994) Translation of Sindbis virus mRNA: effects of sequences downstream of the initiating codon. J Virol. 68:8111–7.

Gardner et al., (2000) Infection of human dendritic cells by a sindbis virus replicon vector is determined by a single amino acid substitution in the E2 glycoprotein. J Virol. 74:11849–57.

Kuhn et al., (1991) Infectious RNA transcripts from Ross River virus cDNA clones and the construction and characterization of defined chimeras with Sindbis virus. Virology 182:430–441.

Moncayo et al., (2001) Genetic diversity and relationships among Venezuelan equine encephalitis virus field isolates from Colombia and Venezuela. Am J Trop Med Hyg. 65:738–46.

Monroe and Schlesinger, (1984) Common and distinct regions of defective-interfering RNAs of Sindbis virus. J. Virol. 49:865–872.

Monroe and Schlesinger, (1983) RNAs from two independently isolated defective interfering particles of Sindbis virus contain a cellular tRNA sequence at their 5' ends. Proc. Natl. Acad. Sci. USA. 80:3279–3283.

Pushko et al., (1997) Replicon-helper systems from attenuated Venezuelan equine encephalitis virus: expression of heterologous genes in vitro and immunization against heterologous pathogens in vivo. Virology. 239:389–401.

Weiss and Schlesinger, (1991) Recombination between Sindbis virus RNAs J. Virol. 65:4017–4025.

Weiss et al., (1989) Evidence for specificity in the encapsidation of Sindbis virus RNAs. J. Virol. 63:5310–5318.

Any patents or publications mentioned in this specification are indicative of the levels of those skilled in the art to which the invention pertains. Furthermore, these patents and publications are incorporated by reference herein to the same extent as if each individual publication was specifically and individually indicated to be incorporated by reference.

What is claimed is:

1. A method of producing packaged alphavirus particles, comprising the steps of:
(a) transfecting a first set of cells with (i) a Sindbis virus replicon comprising a sequence encoding a nonstructural protein nsp2 that comprises an amino acid selected from the group consisting of proline, leucine, glycine and valine at amino acid position 726; (ii) a first helper RNA comprising a sequence encoding an alphavirus capsid protein and cis-acting elements that allow efficient replication and packaging of said first helper RNA and (iii) a second helper RNA comprising a sequence encoding the alphavirus glycoproteins E1 and E2 and cis-acting elements that allow efficient replication and packaging of said second helper RNA;
(b) obtaining a primary stock of viral particles comprising
(i) viral particles containing said Sindbis virus replicon,
(ii) viral particles containing said first helper RNA, and
(iii) viral particles containing said second helper RNA;
(c) infecting a second group of cells with said primary stock of viral particles at high multiplicity of infection; and
(d) obtaining a larger secondary stock of packaged viral particles comprising (i) viral particles containing said Sindbis virus replicon, (ii) viral particles containing said first helper RNA, and (iii) viral particles containing said second helper RNA, wherein said secondary stock has a titer of packaged replicons at least $1\times10^8$ infectious units/ml.

2. The method of claim 1, further comprising the steps of:
   (a) infecting a third group of cells with said secondary stock of viral particles at a high multiplicity of infection; and
   (b) obtaining a larger stock of viral particles comprising (i) viral particles containing said Sindbis virus replicon, (ii) viral particles containing said first helper RNA, and (iii) viral particles containing said second helper RNA, wherein said stock has a titer of packaged replicons at least $1\times10^8$ infectious units/ml.

3. The method of claim 1, wherein said Sindbis virus replicon and said first and second helper RNAs are delivered to the cells in plasmid form or in RNA form.

4. The method of claim 1, wherein sequences encoding said capsid protein and glycoproteins are from an aiphavirus selected from the group consisting of Sindbis virus, Venezuelan Equine encephalitis virus, Ross River virus, and Semliki Forest virus.

5. The method of claim 1, wherein said cis-acting elements comprise tRNA$^{Asp}$ and the replicational enhancer of Sindbis virus.

6. A method of generating viral particles containing Sindbis virus replicons for production of recombinant protein, comprising the steps of:
   (a) transfecting a first group of cells with (i) a Sindbis virus replicon comprising a sequence encoding a heterologous protein and a sequence encoding a nonstructural protein nsP2 that comprises an amino acid selected from the group consisting of proline, leucine, glycine, and valine at amino acid position 726; (ii) a first helper RNA comprising a sequence encoding an alphavirus capsid protein and cis-acting elements that allow efficient replication and packaging of said first helper RNA and (iii) a second helper RNA comprising a sequence encoding the alphavirus glycoproteins E1 and E2 and cis-acting elements that allow efficient replication and packaging of said second helper RNA;
   (b) obtaining a primary stock of viral particles comprising (i) viral particles containing said Sindbis virus replicons comprising a sequence encoding said heterologous protein, (ii) viral particles containing said first helper RNA, and (iii) viral particles containing said second helper RNA;
   (c) infecting a second group of cells with said primary stock of viral particles at high multiplicity of infection;
   (d) obtaining a secondary, larger stock of viral particles comprising (i) viral particles containing said Sindbis virus replicons comprising a sequence encoding said heterologous protein, (ii) viral particles containing said first helper RNA, and (iii) viral particles containing said second helper RNA, wherein said secondary stock has a titer of packaged replicons of at least $1\times10^8$ infectious units/ml; and
   (e) infecting host cells with the viral particles of (d) to produce said heterologous protein encoded by said packaged replicons.

7. The method of claim 6, wherein said host cells are mammalian cells or insect cells.

8. The method of claim 6, wherein said Sindbis virus replicon and said first and second helper RNAs are delivered to the cells in plasmid form or in RNA form.

9. The method of claim 6, wherein sequences encoding said capsid protein and glycoproteins are from alphavirus selected from the group consisting of Sindbis virus, Venezuelan Equine encephalitis virus, Ross River virus, and Semliki Forest virus.

10. The method of claim 6, wherein said cis-acting elements comprise tRNA$^{Asp}$ and the replicational enhancer of Sindbis virus.

11. The method of claim 1, wherein aid Sindbis virus replicon further comprises a structural RNA element that increases RNA translation efficiency.

12. The method of claim 11, wherein said structural RNA element is a G-C rich sequence located 28 nucleotides downstream from an initiating AUG of Sindbis virus subgenomic RNA.

13. The method of claim 6, wherein said Sindbis virus replicon further comprises a structural RNA element that increases RNA translation efficiency.

14. The method of claim 13, wherein said structural RNA element is a G-C rich sequence located 28 nucleotides downstream from an initiating AUG of Sindbis virus subgenomic RNA.

* * * * *